US012763216B2

(12) United States Patent
Ravishankar et al.

(10) Patent No.: US 12,763,216 B2
(45) Date of Patent: Oct. 13, 2026

(54) SYSTEMS AND METHODS TO DETECT A FALSE ALARM IN A PATIENT MONITORING DEVICE

(71) Applicant: GE Precision Healthcare LLC, Wauwatosa, WI (US)

(72) Inventors: Hariharan Ravishankar, Bangalore (IN); Rohan Patil, Bangalore (IN); Abhijit Patil, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 174 days.

(21) Appl. No.: 18/312,919

(22) Filed: May 5, 2023

(65) Prior Publication Data

US 2023/0386676 A1 Nov. 30, 2023

(30) Foreign Application Priority Data

May 25, 2022 (IN) ............................ 202241029900

(51) Int. Cl.

| | |
|---|---|
| ***G16H 50/30*** | (2018.01) |
| ***G06N 3/04*** | (2023.01) |
| ***G06N 3/08*** | (2023.01) |
| ***G16H 40/60*** | (2018.01) |

(52) U.S. Cl.

CPC ............... *G16H 50/30* (2018.01); *G06N 3/04* (2013.01); *G06N 3/08* (2013.01); *G16H 40/60* (2018.01)

(58) Field of Classification Search

CPC ........ G16H 50/30; G16H 40/60; G16H 15/00; G16H 50/70; G16H 40/63; G16H 40/67; G16H 50/20; G06N 3/04; G06N 3/08; G06N 3/045

See application file for complete search history.

(56) References Cited

U.S. PATENT DOCUMENTS

2012/0330227 A1* 12/2012 Budiman ............ A61B 5/4839 604/66
2015/0364022 A1* 12/2015 Dyell ..................... G16H 40/63 340/573.1
2020/0038671 A1* 2/2020 Schulhauser ........ A61B 5/7275
2023/0306267 A1* 9/2023 Jacob Banville .... G06N 3/0464

* cited by examiner

*Primary Examiner* — Chad A Newton

(57) ABSTRACT

The disclosure relates generally to a patient monitoring device and, more particularly, to improved system and method to detect a false alarm in a patient monitoring device. The disclosure specifically relates to a system and a method to detect a false alarm in a patient monitoring device. The system may include a patient monitoring device configured to receive a patient monitoring data from a patient. The system may enable the processing of the patient monitoring data by a processing device to determine a false alarm generated by the patient monitoring device. The system may further provide a user-interface, which may be configured to filter a true alarm from a false alarm generated by the patient monitoring device.

14 Claims, 9 Drawing Sheets

SYSTEMS AND METHODS TO DETECT A FALSE ALARM IN A PATIENT MONITORING DEVICE

CROSS-REFERENCE TO RELATED APPLICATIONS

The present matter claims priority to Indian Patent Application No. 202241029900, titled "SYSTEMS AND METHODS TO DETECT A FALSE ALARM IN A PATIENT MONITORING DEVICE," filed May 25, 2022, the contents of which are incorporated by reference herein.

FIELD

This disclosure relates generally to patient monitoring device and, more particularly, to improved system and method to detect a false alarm in a patient monitoring device.

BACKGROUND

Clinical alarm system of a medical device is an automatic warning system aimed at drawing the hospital staff's attention. The clinical alarm system gets triggered by a physiological change in the subject's body (patient's body) and when an upper threshold or a lower threshold of the physiological parameter gets breached. The clinical alarm system of the medical device may have one or more levels of alarms indicating various situations such as life-threatening situation, device malfunction, imminent danger, unsafe situation etc.

The diverse medical devices responsible for generating auditory clinical alarms may include infusion pumps, mechanical ventilators, continuous renal replacement therapy machines (CRRT), defibrillators, heating/cooling systems, intermitted pneumatic compression devices, ultrasound, humidifiers, and blood refrigerators, EEG (Electroencephalogram), ECG (Electrocardiogram) and other long term monitoring devices and short-term diagnostic devices etc.

With the improvement in the medical devices and introduction of new medical devices, the number of clinical alarms generated from any new medical device is also increasing. The clinical alarms have now become a new problem for the hospital staff. This has resulted in increase in fatigue (also called as alarm hazard) due to false alarms. Further, due to the false alarm, a patient runs a high risk of not getting medical emergency attention as the hospital staff, often, fail to identify or to differentiate the false alarm from the genuine alarm, which demands the attention of the hospital staff to attend a patient in need. This threatens the life of the patient and puts them under high risk of not getting medical attention or patient care at the right time.

The alarm fatigue leads to desensitization of the hospital staff to the critical alarms due to sensory overload caused from the large number of false alarm and hence defeating the purpose of the alarm system in the medical devices. Majority of these alarms falls into a category of false alarm and approximately five percent of the alarms require medical intervention to avoid patient harm.

Another challenge associated with the false alarm generated by the medical devices is the signal arising from poor sensing. The false alarms are often caused by patient motion, poor sensor placement, intermittent cables, and limitations in the alarm detection algorithm. If the sensors provided in the medical devices are not properly attached or maintained, the false alarm persists e.g., if a particular electrode of a medical device is not functioning properly and despite knowing the fact, the medical devices are not provided with any means to disable the alarm system of the medical device or any substitute to overcome the malfunction in the medical device.

Each medical device has its own unique configurations and settings for the alarm. The major challenge lies in designing an alarm system, which would cater to every patient's requirement considering the physiological conditions of each of the patients. In practical world, none of the patients have same or similar physiological conditions. But the state-of-the-art alarm systems in the medical devices are designed and configured for homogeneous conditions and completely disregards inter-patient heterogeneity.

Existing alarm system for medical devices are inherently rule-based engines, which map patho-physiological causes to ranges of values on monitoring signals such as hypoxemia leading to Spo2 (saturation of peripheral oxygen) less than 90 percent, triggers the alarm system of the medical device. However, normal ranges across can vary across patients depending upon their clinical history, medication, genetics etc. For example, irregular morphology in an ECG or moderate tachycardic rhythms might be a normal for patient with cardiac disease history. There are no means available in the available technologies, which would allow the hospital staff to tune the medical device according to the present health condition of the patient. A patient with a pacemaker, if admitted to a hospital, the alarm system of the medical device may get triggered and generate incessant number of alarms even though the patient may not require any medical attention.

Hence, there is a need for a system and method, which can detect a false alarm in a medical device and help in reducing the fatigue caused by the non-life-threatening alarms and at the same time generate a true alarm, which would indicate a condition demanding the clinician's or a hospitals staff's attention. Based on the available physiological information related to the patient, the clinician may deem an alarm generated by the alarm system of the medical device as a false alarm or a true alarm.

SUMMARY OF THE INVENTION

This summary introduces concepts that are described in more detail in the detailed description. It should not be used to identify essential features of the claimed subject matter, nor to limit the scope of the claimed subject matter. Its sole purpose is to present concepts in a simplified form as a prelude to the more detailed description that is presented later.

In accordance with an aspect of the disclosure, a system to detect a false alarm in a patient monitoring device may be provided. The system may comprise a patient monitoring device configured to receive a patient monitoring data from a subject's body. The system may comprise a data processing device connected to the patient monitoring device. The data processing device may be configured to receive the patient monitoring data from the patient monitoring device. The system may enable the processing of the patient monitoring data by the processing device to determine a false alarm generated by the patient monitoring device. The system may further provide a user-interface, which may be configured to filter a true alarm from a false alarm generated by the patient monitoring device.

In accordance with an aspect of the disclosure, a method to detect a false alarm in a patient monitoring device may be provided. Further, the method provides, receiving a patient monitoring data from a patient monitoring device. The method may further provide processing the received patient monitoring data to determine a false alarm generated by the patient monitoring device. The method may compare one or more data sets stored in a patient specific data bank with the patient monitoring data and filtering a false alarm from a true alarm by enabled by a user-interface.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

The figures are not scale. Wherever possible, the same reference numbers will be used throughout the drawings and accompanying written description to refer to the same or like parts.

DETAILED DESCRIPTION

Figure 1:
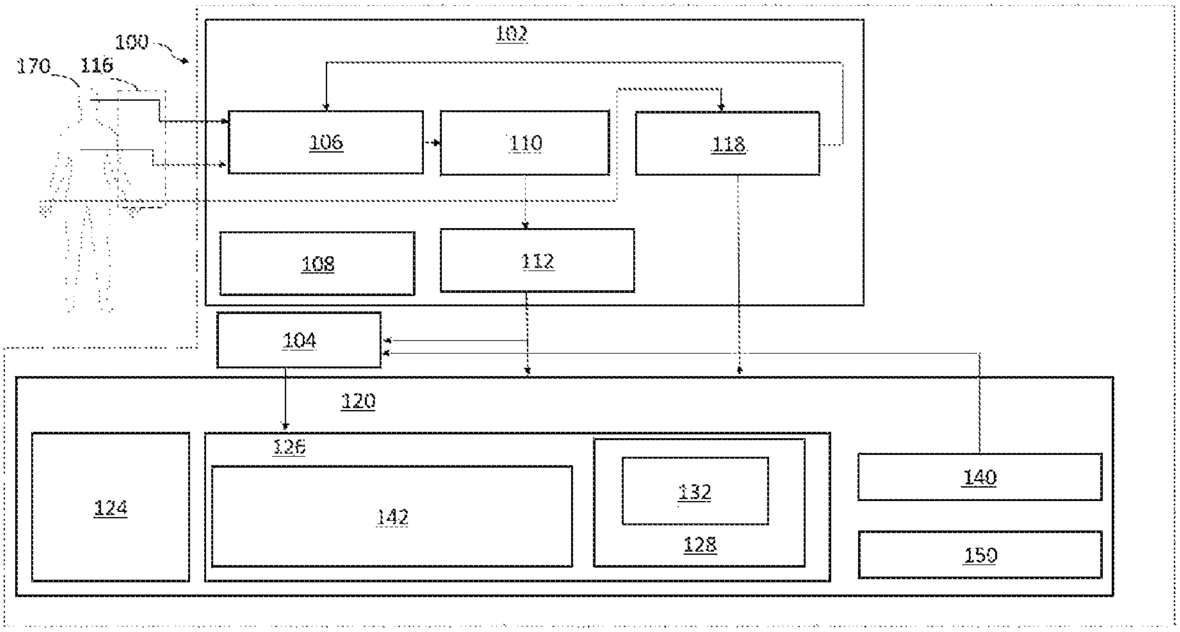
FIG. 1 illustrate a system that for acquisition of multi-modal data of a subject.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles “a,” “an,” “the,” and “said” are intended to mean that there are one or more of the elements. The terms “comprising,” “including,” and “having” are intended to be inclusive and mean that there may be additional elements other than the listed elements.

As used herein, the term “computer” and related terms, e.g., “computing device”, “computer system” “processor”, “controller” are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as “about” and “substantially”, are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms “systems”, “devices” and “apparatuses are interchangeable and include components, sub-components, sub-systems that include without limitation the medical imaging devices.

The term “source model” or “a machine learning model” or a “machine learning module” is used herein to refer to an AI/ML model configured to perform a signal processing or analysis task on quasi-stationary signals. The signal processing or analysis task can vary. In various embodiments, the signal processing or analysis task can include, (but is not limited to): a segmentation task, an image reconstruction task, an object recognition task, a motion detection task, a video tracking task, an optical flow task, an attention region identification task, an object labeling task and the like. The source model can employ various types of AI/ML algorithms, including (but not limited to): deep learning models, neural network models, deep neural network models (DNNs), convolutional neural network models (CNNs), and the like.

While certain examples are described below in the context of medical or healthcare systems, other examples can be implemented outside the medical environment.

In accordance with an aspect of the disclosure, a system to detect a false alarm in a patient monitoring device may be provided. The system may comprise a patient monitoring device configured to receive a patient monitoring data from a subject’s body. The system may comprise a data processing device connected to the patient monitoring device. The data processing device may be configured to receive the patient monitoring data from the patient monitoring device. The system may enable the processing of the patient monitoring data by the processing device to determine a false alarm generated by the patient monitoring device. The system may further provide a user-interface, which may be configured to filter a true alarm from a false alarm generated by the patient monitoring device.

In accordance with an aspect of the disclosure, a method to detect a false alarm in a patient monitoring device may be provided. Further, the method provides, receiving a patient monitoring data from a patient monitoring device. The method may further provide processing the received patient monitoring data to determine a false alarm generated by the patient monitoring device. The method may compare one or more data sets stored in a patient specific data bank with the patient monitoring data and filtering a false alarm from a true alarm by enabled by a user-interface.

According to an aspect of the disclosure, FIG. 1 illustrates a system 100 that may be used to acquire multi-modal data, including but not limited to data from ultrasound device, CT (Computed Tomography) scanner, MR (Magnetic resonance) machines, ECG (Electrocardiogram), oximeter, infusion pump, bedside monitors. The system 100 comprises a patient monitor device 102. The patient monitoring device 102 may be connected to a data processing device 120. The data processing device 120 may be configured to receive one or more patient monitoring data 116 from the patient monitoring device 102. The patient monitoring device 102 is configured to measure and store a recording of the subject's body vitals like temperature, heart rate, Blood pressure, oxygen saturation level etc. In an embodiment the patient monitoring device 102 may be ECG (Electrocardiogram). The ECG may include a plurality of electrodes (not shown) including a right arm electrode, a left arm electrode, and leg electrode, which are attached to the patient 170 via adhesive pads and/or electrically conductive gel.

In accordance with an example, another embodiment of the disclosure may comprise an oximeter device. The oximeter device may be securely applied to a fingertip of the patient 170. The fingertip may illuminate by red and infrared light, depending on the oxygenated blood content either red or infrared light may be detected by a photodetector. The photodetector may be electrically connected to the data processing device 120 through a data acquisition module 106. The data acquisition module 106 may filter the noise from patient monitoring data 116 collected by the sensing device like photo diodes or the plurality of electrodes interactively connected to the human body. The data acquisition module 106 may also have analog to digital convertor to convert the analog signals into digital signals and a transistor-based circuit e.g., an amplifier to amplify the signals received from the sensors 118. The data acquisition module 106 may be connected to a data storage 110. The data processing device 120 may be configured to receive the filtered patient monitoring data 116 from the data acquisition device 102 via a communication sub system 112 to process the analog signal received form the photodetector and filter and process into a digital signal. The communication between the data processing device 120 and the data acquisition module 106 may be established via a wired medium such as an electrical wire or a wire cable or wireless medium including but not restricted to Bluetooth, Wi-fi etc. In one embodiment, the communication between the data processing device 120 and the data acquisition module 106 may be enabled to a real-time communication. As used herein, the term "real-time" refers to a process executed without any intentional delay.

According to an aspect of the disclosure, the communication subsystem 112 may reversibly communicably couple the patient monitoring device 102 and the data processing device 120. The data processing device 120 may be connected either directly to the data acquisition module 106 or indirectly to the data acquisition module via data storage 110. The patient monitoring data 116 acquired by the patient monitoring device 102 may be stored in the data storage 110 and transferred to the data processing device 120. The patient monitoring device 102 may comprise an energy storage subsystem 108, wherein electrical energy may be stored, enabling the patient monitoring device 102 to operate while the taking data from the subject. In some embodiment, the energy storage subsystem 108 may comprise a replaceable or non-replaceable rechargeable battery.

According to an aspect of the disclosure, the data processing device 120 may comprise a non-transitory data memory 126, wherein the data indicative of the subject's vitals acquired by the patient monitoring device 102 may be stored. In some embodiments, the data memory 126 may comprise a memory card, a flash drive, or a removable hard driver. In some embodiment the data processing device 120 may be integrated into the patient monitoring device 102 and the integrated patient monitoring device 102 may have a common memory unit. In an embodiment, the data memory 126 of the processing device may comprise a patient specific data bank 142. The patient specific data bank 142 may be repository of history of each subject and the health-related data sets of each of those subjects. The patient specific data bank 142 may comprise a relational database management system (RDMS) comprising a collection program capable of storing the subject's data in form of tables and the data provided in the table can be fetched using a structured query language. The tables may have rows and columns, which can be accessed for adding, editing, deleting the records of the subject. The subject's data stored in the patient specific data bank 142 may include the name, age, previous clinical tests and results. In some embodiments, the data processing device 120 may receive the patient monitoring data 116 from a plurality of data sources, including one or more network devices. Data sets stored within the patient specific data bank 142 may be organized according to one or more known organizational schemes or configured into one or more known data structures. In some embodiments, the patient monitoring data 116 and vital sign data may be stored in the patient specific data bank 142 by indexing the data according to patient, acquisition time, originating monitor ID, and so forth.

In accordance with yet another aspect of the disclosure, the data processing device 120 may comprise a processor 124 configured to execute machine readable instructions stored in the data memory 126. The processor 124 may be single core or multi-core, and the programs executed thereon may be configured for parallel or distributed processing. In some embodiments, the processor 124 may optionally include individual components that are distributed throughout two or more devices, which may be remotely located and/or configured for coordinated processing. In some embodiments, one or more aspects of the processor 124 may be virtualized and executed by remotely-accessible networked computing devices configured in a cloud computing configuration. In some embodiments, the data memory 126 may include components disposed at two or more devices, which may be remotely located and/or configured for coordinated processing. In some embodiments, one or more aspects of the non-transitory memory 126 may include remotely accessible networked storage devices configured in a cloud computing configuration.

In accordance with another aspect of the disclosure, the data memory 126 may store a machine learning module 128, which may include neural networks and the neural networks may be having several neural network layers. The machine learning module 128 further comprises a contrastive training module 132. The contrastive training module 132 may be trained to predict a false alarm generated by the patient monitoring device 102. Although the example illustrated in FIG. 1 shows the contrastive training module 132 stored in the data memory 126, non-transitory memory, in other embodiments, the contrastive training module 132 may be stored in a different memory that is not integral to the data processing device 120. The contrastive training module 132 may comprise machine executables instructions for training one or more of the neural networks stored in the machine leaning module 128. In one embodiment the contrastive training module 132 may include time-contrastive learning models.

The machine learning module 128 may include trained and/or untrained neural networks and may further include various neural network metadata pertaining to the trained and/or untrained networks. In some embodiments, the neural network metadata may include an indication of the training data used to train each neural network, a training method employed to train each neural network, an accuracy/validation score of each neural network, and a type of use-case/protocol for which the trained neural network may be applied.

In accordance with an another aspect of the disclosure, the patient monitoring device 102 and the data processing device 120 may be connected to a user-interface 104 and the user-interface 104 may be configured to receive the patient monitoring data 116 from the patient monitoring device 102. The user-interface 104 may comprise a processor. The user-interface 104 may comprise a human in loop system configured to receive an input from a user input device 140 interactively operable by a user i.e. a human being. The user input device 140 may comprise one or more of a touch-screens, a keyboard, a mouse, a trackpad, a motion sensing camera, or other device configured to enable the user to enter, interact with, and/or manipulate, data received from the patient monitoring device 102. wherein the user-interface is connected to patient monitoring device and the data processing device through a wired means or a wireless means.

In accordance with another aspect of the disclosure, the data processing device may comprise an output device 150, which may include a visual alarm such as LED lights, then an audio alarm such as a sound transducer. The output device 150 may generate the false alarm to alert the clinician.

Figure 2:
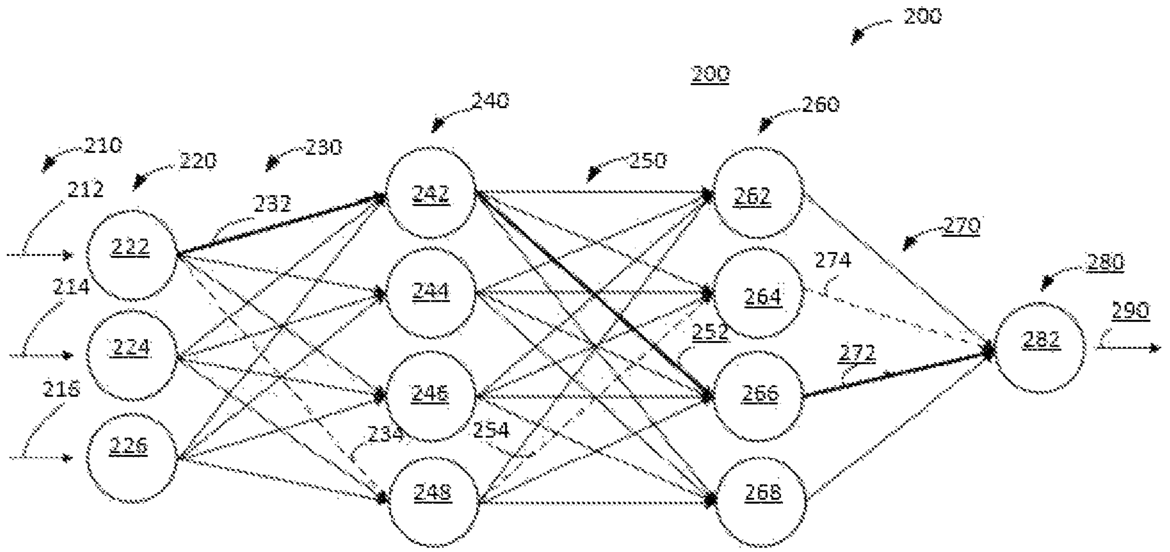
FIG. 2 illustrates an example of a learning neural network.

In accordance with an aspect of the disclosure, FIG. 2 illustrates an example of a learning neural network 200. The example neural network 200 includes layers 220, 240, 260, and 280. The layers 220 and 240 are connected with neural connections 230. The layers 240 and 260 are connected with neural connections 250. The layers 260 and 280 are connected with neural connections 270. Data flows forward via inputs 212, 214, 216 from the input layer 220 to the output layer 280 and to an output 390. The inputs 212, 214, 216, as per the present disclosure, can be patient monitoring data 116 received from the patient monitoring device 102. For every patient monitoring data 116 an alarm may be generated, and the generation of the alarm may be based on the threshold set in the patient monitoring device 102.

The layer 220 is an input layer that includes a plurality of nodes 222, 224, 226. The layers 240 and 260 are hidden layers and include nodes 242, 244, 246, 248, 262, 264, 266, 268. The neural network 200 may include more or less hidden layers 240 and 260 than shown. The layer 280 is an output layer and includes a node 282 with an output 290. Each input 212-216 corresponds to a node 222-226 of the input layer 220, and each node 222-226 of the input layer 220 has a connection 230 to each node 242-248 of the hidden layer 240. Each node 242-248 of the hidden layer 240 has a connection 250 to each node 262-268 of the hidden layer 260. Each node 262-268 of the hidden layer 260 has a connection 270 to the output layer 280. The output layer 280 has an output 290 to provide an output from the example neural network 200.

Of connections 230, 250, and 270 certain example connections 232, 252, 272 may be given added weight while other example connections 234, 254, 274 may be given less weight in the neural network 200. Input nodes 222-226 are activated through receipt of input data via inputs 212-216, for example. Nodes 242-248 and 262-268 of hidden layers 240 and 260 are activated through the forward flow of data through the network 200 via the connections 230 and 250, respectively. Node 282 of the output layer 280 is activated after data processed in hidden layers 240 and 260 is sent via connections 270. When the output node 282 of the output layer 280 is activated, the node 282 outputs an appropriate value based on processing accomplished in hidden layers 240 and 260 of the neural network 200.

Figure 3:
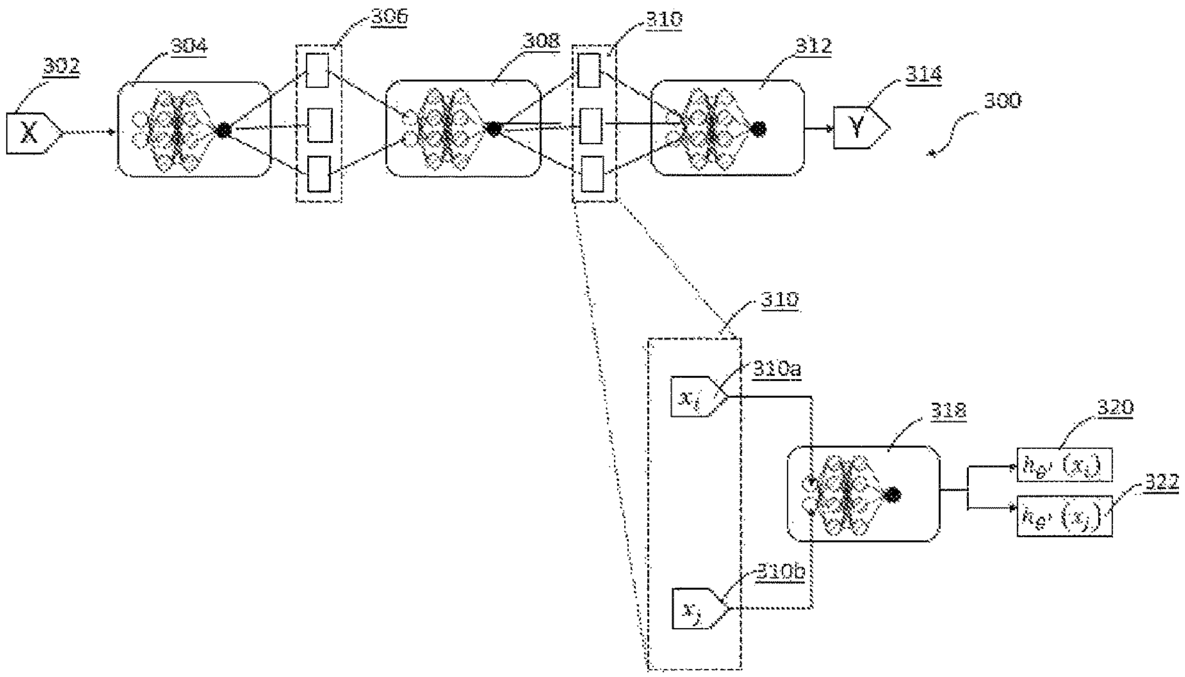
FIG. 3 illustrates a contrastive neural network of a contrastive training module.

In accordance with an aspect of the disclosure, FIG. 3 illustrates a contrastive neural network 300 of a contrastive training module 132. The contrastive neural network 300 includes layers 304, 308 and 310. The layers 304 may be the input layer and the layer 312 may be an output layer. The input layer 304 being configured to receive an input 302 and the output layer 312 being configured to generate an output 314. The input 302 can be a patient monitoring data 116, which may be received from the patient monitoring device 102.

Each of the layers 304, 308 and 312 of the contrastive neural network 300 may be configured to receive an input, which may be first generated as an output 306, 310 and 314 from the previous layer, with an exception of the first layer 304. Between each of the layers 304,308 and 312 of the contrastive neural network 300, an intermediate representation is extracted. In an embodiment the intermediate representations may be the outputs generated by an intermediate layer 308 of the contrastive neural network 300 and in another embodiment the intermediate representation may be an output generated by one of the layer of the contrastive neural network 300 with the exception of the output 314 generated by the output layer 312 of the contrastive neural network 300.

The contrastive training module 132 is an artificial intelligence (AI) module, which may be operably configured to get trained and compare at least two intermediate representations obtained from the intermediate layer 308 of the contrastive neural network 300. The contrastive training module 132 may have one or more such contrastive neural network 300. The intermediate representation can be called as a vector.

In accordance to an another aspect of the disclosure, the contrastive training module 132 may be trained and configured to receive and compare the intermediate representations to generate a contrastive loss in order to determine the similarities between the intermediate representations. The contrastive learning of the contrastive neural network 300 may indicate if two or more inputs are similar, then, the features of the inputs may also be similar.

According to an aspect of the disclosure, the intermediate representation may be obtained from the patient monitoring data 116, which is essentially in form of a signal. In an embodiment, to generate the contrastive loss, the intermediate representations 310*a*, 310*b* of the patient monitoring data 116 are processed in a layer 318 to generate projections 320,322, which are processed for determining the similarity. In an embodiment, the $x_i$ may be indicative of a data sample stored in the patient specific data bank 142 and the $x_i$ may be indicative of a data sample taken from the patient monitoring data 116.

The projections 320, 322 compared to determine the contrastive loss (d). The contrastive loss (d) may indicate the resemblance of the projections 320,322 generated by the layer 318. More the contrastive loss (d), lesser the resemblance between the projections 320, 322 and if lesser the contrastive loss (d), more the resemblance between the projections 320,322. One of the projections 320,322 may indicate the patient monitoring data 116 and the other projection 320,322 may indicate a data set stored within the patient specific data bank 142. Since, the nature of the data may comprise quasi-stationary signal such as blood pressure, ECG signals etc., the contrastive neural network 300 may be a time-contrastive learner. In terms of time series signals, if at least two data samples are nearby at a given time interval or if the time (t) and time (τ), of the two data samples, are in proximity, then it may be assumed that the corresponding intermediate representations of the samples may be similar.

$f_{\theta}$: x→y, (Full networks), $h_{\theta'}$: x→z (intermediate representations)

If $x_i$ and $x_j$ are similar, d $(h_{\theta'}(x_i), h_{\theta'}(x_j))<\beta$, d is the contrastive loss.

$d(h_{\theta'}(x(t)), h_{\theta'}(x(\tau)))$, if $|t-\tau|\leq w$

During deployment, evaluate $d(h_{\theta'}(x^p(t)), h_{\theta'}(\{x^p(\tau)\}))$, where $\{x^p(\tau)\}$ may be a user-interface selected false alarms for the subject p.

$x_i$ and $x_j$ may be indicative of a data sample of a patient data collected for the training of the contrastive neural network 300 and the samples $x_i$ and $x_j$ may be passed through the a contrastive neural network 300. $h_{\theta'}$ may indicate the contrastive neural network 300. The d $(h_{\theta'}(x_i), h_{\theta'}(x_j))<\beta$ may indicate that both the samples $x_i$ and $x_j$ may be compared by the contrastive neural network 300, mathematically represented as $h_{\theta'}$. The $h_{\theta'}$ may be a feature extractor, which extracts the features from the samples in form of vectors (or projections or intermediate representations). A distance 'd.' between the samples $x_i$ and $x_j$ may be determined after generating vectors for both the samples. β may represent a threshold value for measuring the contrastive loss (d). If the distance 'd.' between the intermediate representations of the data samples is less than β, then the samples $x_i$ and $x_j$ may have proximity indicating similarities between the samples $x_i$ and $x_j$ and if the distance 'd.' is greater than β, then the samples $x_i$ and $x_j$ may not have similarities. The $h_{\theta'}$ may indicate the contrastive neural network 300 during training phase and the trained $h_{\theta'}$ contrastive neural network 300 may be deployed during the clinical scenario.

During the clinical scenario, the patient monitoring data 116 may be indicated by the $x^p(t)$ and the data stored in the patient specific data bank 142 may be indicated by $x^p(\tau)$. The $d(h_{\theta'}(x^p(t)), h_{\theta'}(\{x^p(\tau)\})$ may indicate the comparison being done by the trained contrastive neural network 300 to determine the proximity between the patient monitoring data 116 and the data stored in the patient specific bank 142.

Figure 4:
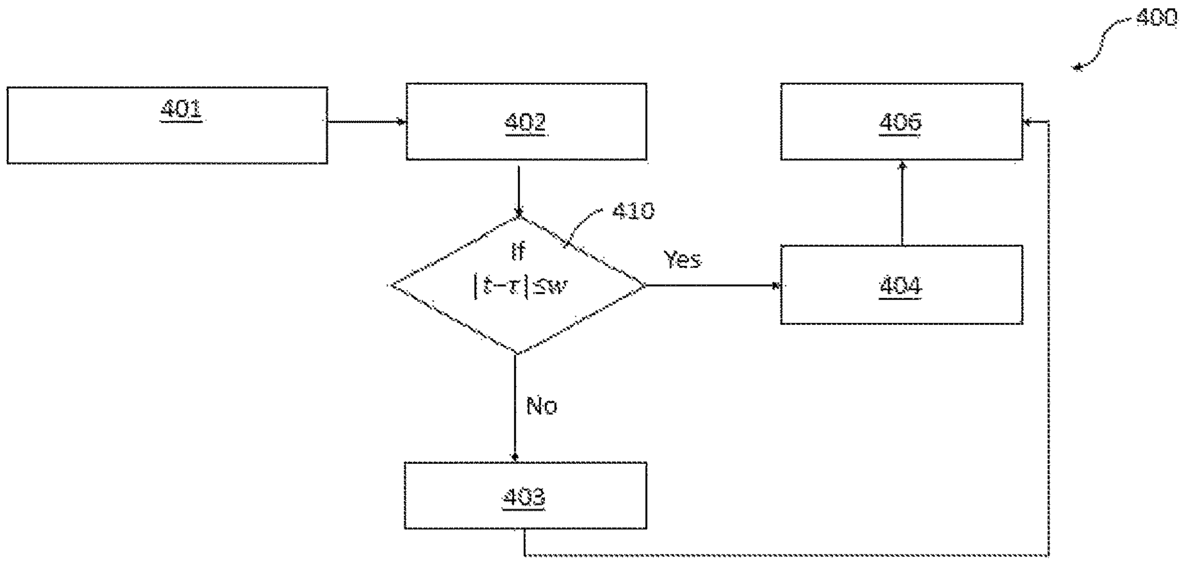
FIG. 4 illustrates a block diagram depicting an embodiment for a time-contrastive learning and measuring the contrastive loss.

In accordance with an aspect of the disclosure, FIG. 4 illustrates block diagram 400 depicting an embodiment for a time-contrastive learning/training of the contrastive neural network 406. A data sample collection 401 comprising data related to different patients and their body vitals like blood pressure, oxygen saturation, respiration rate, body temperature etc. A sample pair 402 may be selected from the data sample collection 401. The sample pair 402 are compared 410 in the contrastive neural network 406 for training and determine the proximity between the samples. If the result, after the comparing the data samples, is a positive sample 404, then there may exist proximity between the sample pair 402 i.e. the difference in the time stamps of both the samples is less than a predetermined value (w) and if the result is a negative sample 403, then there is no proximity between the sample pair 402 i.e. the difference in the time stamps of both the samples is greater than the predetermined value (w). Proximity between the samples may indicate the similarity in the features of the selected pair of samples. This determination of the similarity between the data samples may enable the identification of the false alarm generated by the patient monitoring device 102.

For determining the proximity among a selected pair of samples, the contrastive loss ($|t-\tau|$), in terms of time period, may be less than a predetermined value (w), wherein the time 't' indicates the time stamp of sample of $x_i$ and time 'τ' indicates time stamp for sample $x_j$. The contrastive neural network 406 gets trained based on the negative 403 and positive samples 404 to identify similar data samples.

Figure 5:
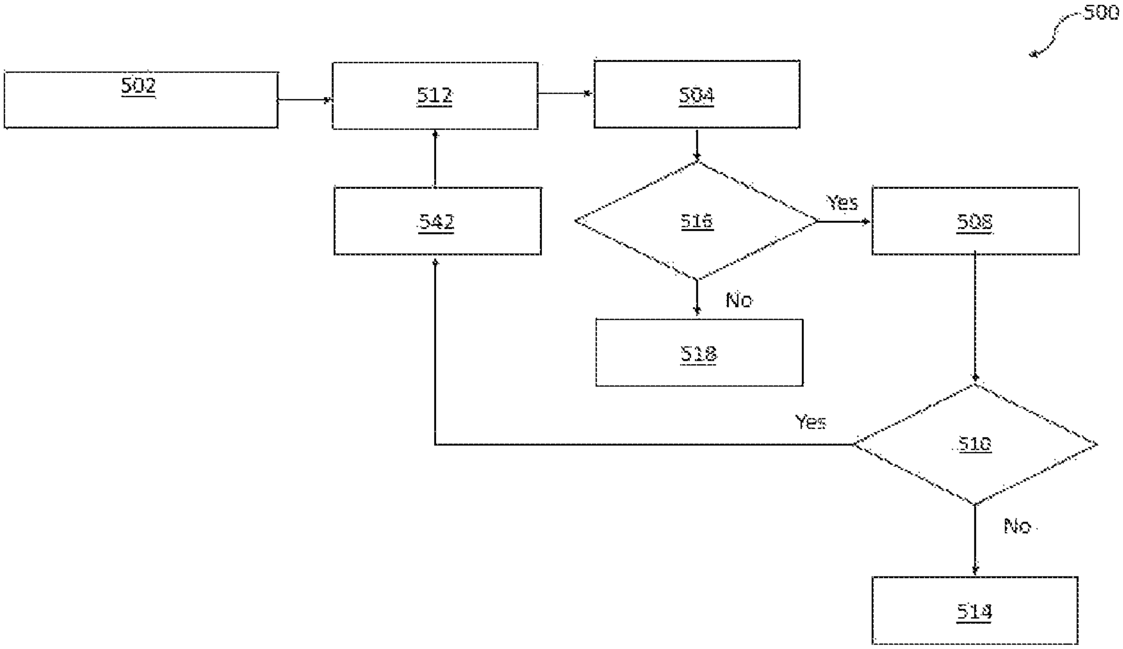
FIG. 5 illustrates a block diagram for the system to detect the false alarm from a patient monitoring device.

In accordance with an aspect of the disclosure, FIG. 5 illustrates a block diagram 500 for the system to detect the false alarm for a patient monitoring device 502. The patient monitoring device 502 generates patient monitoring data 512. The trained contrastive neural network 406 based on the data sample collection 401 may be implemented in a clinical scenario to compare and identify the similar data samples to determine a false alarm. The contrastive neural network 504 may be implemented for a homogeneous data indicative of a specific patient. The contrastive neural network 504 compare the patient monitoring data 512 with the data set stored in the patient specific data bank 542. In another embodiment, when the patient specific data bank 542 is empty then the trained contrastive neural network 504 compares the patient monitoring data 512 based on the data sample collection 401. If the patient monitoring data 512 matches 516 with at least a data set in the patient specific data bank 542, then output indicates a false alarm, which may be modulated 518. If the patient monitoring data 512 does not match with the data set in the patient specific data bank 542, then the human in loop system 508 of the user-interface checks 510 and filters out the data for a false alarm from the true alarm. An alarm signal or an alarm report 514 may be generated for the true alarm by a user output device. For the false alarms filtered by the user-interface 504, the corresponding patient monitoring data 512 may be stored in the patient specific data bank 542.

Figure 6:
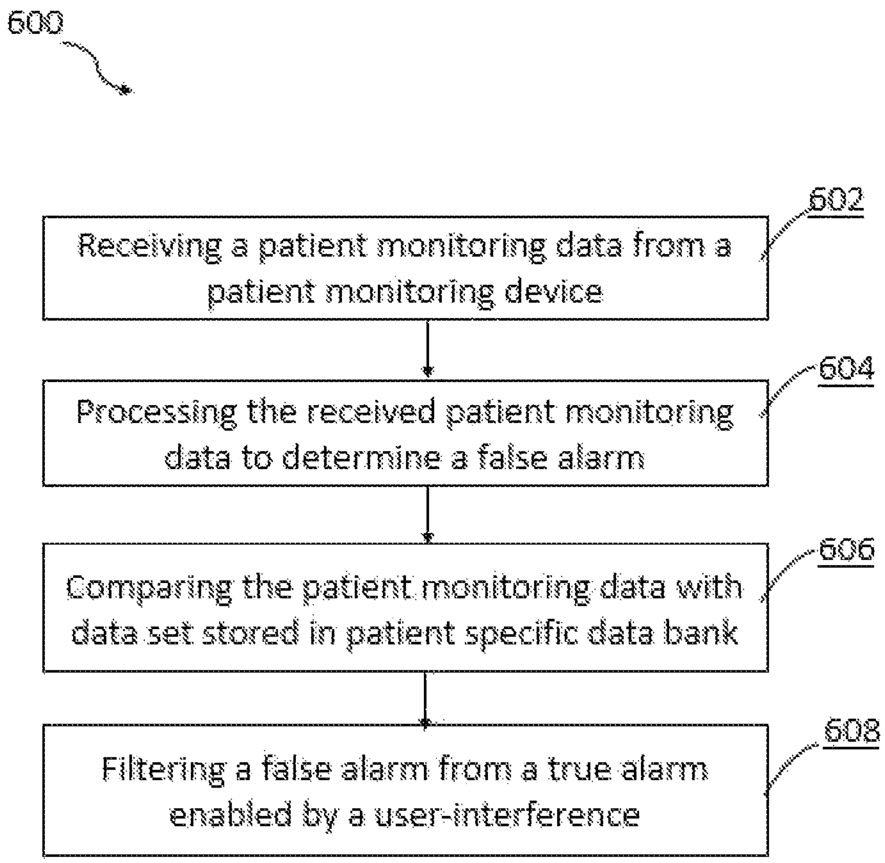
FIG. 6 illustrates a flow chart for a method to detect a false alarm generated by the patient monitoring device.

In accordance with an aspect of the disclosure, FIG. 6 illustrates a flow chart 600 for a method to detect a false alarm generated by the patient monitoring device 102. In step 602, the data processing device 120 may be configured to receive a patient monitoring data 116 from the patient monitoring device 102. The data processing device 120 may be configured to receive the filtered patient monitoring data 116 from the data acquisition device 120 via a communication sub system 112.

The machine learning module 128 in the data memory 126 may comprise a contrastive training module 132, which may be trained based on the data sample collection 401. In an embodiment, the comparison of the patient monitoring data 116 may be done with the subject's existing data related to vitals of the subject stored in the patient specific data bank 142. The contrastive training module 132 may be trained to predict a false alarm generated by the patient monitoring device 102 when the patient monitoring data 116 may have proximity with the, already, stored data in the patient specific data bank 142. The machine learning module 128 may be trained to reduce the generation of false alarm. In one embodiment the contrastive training module 132 may include time-contrastive learning modules.

The received 602 patient monitoring data 116 may be processed by the data processing device 120 having the machine learning module 128 in an embodiment. In another embodiment, the received patient monitoring data 116 may be processed 604 by the machine learning module 128 stored in an another device or a cloud server accessible through a network. Once the patient monitoring data 116 is processed by the data processing device 120, then the patient monitoring data 116 may be compared 606 with the data stored in the patient specific data bank 142. After the comparison of the patient monitoring data 116, a false alarm may be filtered 608 and modulated. The patient monitoring data 116 matching with the data set stored in the patient specific data bank 142 may have contrastive loss less than a threshold value. The patient monitoring data 116, which may have contrastive loss more than the predetermined threshold value as identified by the trained contrastive neural network 300 of the contrastive learning module 132 may be sent to the user-interface 104 for determining the true alarm and the false alarm. The user-interface 104 may enable the determination of the true alarm and the false alarm. The false alarm determined by the user-interface 104 may get stored in the patient specific data bank 142.

Figure 7:
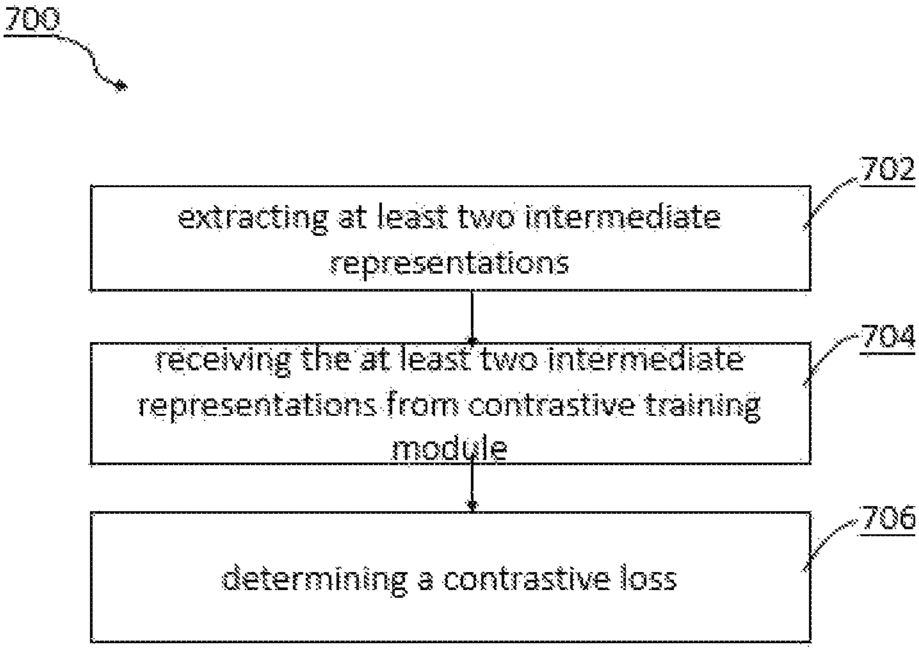
FIG. 7 illustrates a flow chart for the method of processing the patient monitoring data by the data processing device.

In accordance with an aspect of the disclosure, FIG. 7 illustrates a flow chart 700 for the method of processing 604 the patient monitoring data 116 by the data processing device 120. In step 702, the intermediate representations may be extracted. One of the intermediate representations may be indicative of the data set stored in the patient specific data bank 142 and another intermediate representation may be the patient monitoring data 116 received from the patient monitoring device 102.

The contrastive neural network 300 of the contrastive training module 132 may be configured to receive the patient monitoring data 116 as an input. The contrastive neural network 300 may be pre-trained based on the data sample collection 401 collected from several subjects and in an embodiment, the trained contrastive neural network 300 may be the time-contrastive neural network, which may be trained based on the signals of the quasi-stationary in nature. These quasi-stationary signals are indicative of signals generated in a clinical scenario, wherein the signals may be non-stationary signals. The non-stationary signals may have the statistics locally static over a short period of time, but exhibit differences from one local time frame to another such as signals generated by the ECG machine.

The contrastive neural network 300 may have several layers of network and each of the layers may be configured to process the outputs from the preceding layer. From one of the layers of the contrastive neural network 300, an intermediate representation is extracted. In an embodiment the intermediate representations may be the outputs generated by an intermediate layer 308 of the contrastive neural network 300 and in another embodiment the intermediate representation may be an output generated by one of the layer of the contrastive neural network 300 with the exception of the output 314 generated by the output layer 312 of the contrastive neural network 300.

The contrastive training module 132 is an artificial intelligence (AI) module, which may be operably configured to get trained and capable of comparing at least two intermediate representations obtained from the intermediate layer 308 of the contrastive neural network 300. The intermediate representations may be received 704 from the contrastive neural network 300 of the contrastive training module 132 for the purpose of comparing the intermediate representation.

The contrastive loss may be determined 706 by the contrastive training module 132. In accordance with an aspect of the disclosure, the contrastive training module 132 may be trained and configured to generate and compare the intermediate representations to determine a contrastive loss in order to determine the similarities between the intermediate representations. The contrastive learning of the contrastive neural network 300 may indicate if two or more inputs are similar then the features of the inputs may also be similar.

Figure 8:
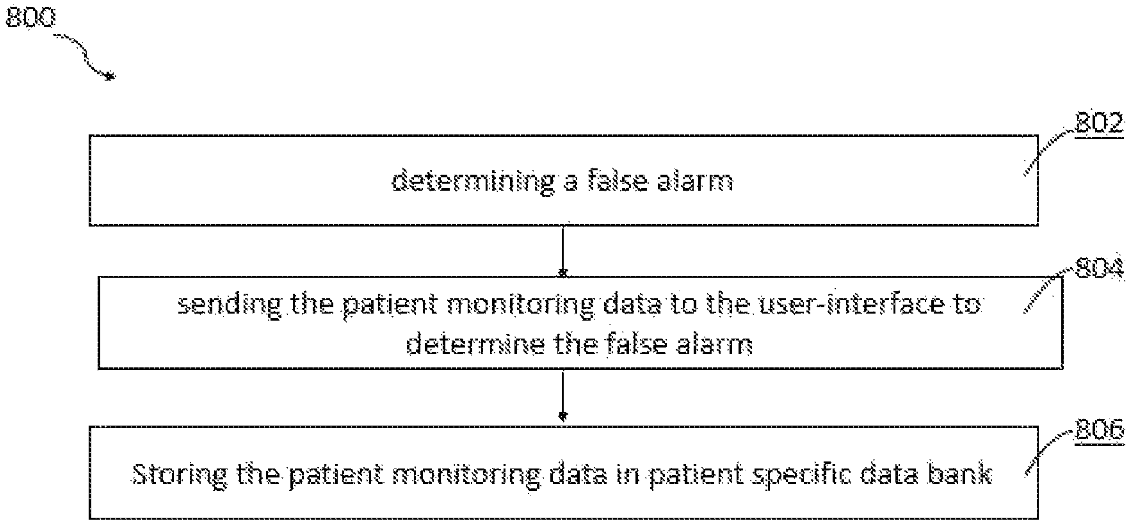
FIG. 8 illustrates a flow chart for the method of comparing the data sets stored in the patient specific data bank with the patient monitoring data.

In accordance with an aspect of the disclosure, FIG. 8 illustrates a flow chart 800 for the method of comparing 606 one or more data sets stored in the patient specific data bank 142 with the patient monitoring data 116. When the patient monitoring data 116 matches with the data set in the patient specific data bank 142, the contrastive loss is less than a threshold value, then a false alarm may be determined 802 by the contrastive neural network 300. This also indicates that the patient monitoring data 116 may be already existing in form of a data set in the patient specific data bank 142. In an embodiment, the determined false alarm may be modulated by attenuating the false alarm using an attenuation circuit. In an embodiment, the attenuation circuit can be an audio attenuator. In an another embodiment, the modulation can be visual indication using a light source such as LED (light emitting diode).

But in a situation, when the contrastive loss may be more than the threshold value, then the patient monitoring data 116 may be sent 804 to the user-interface 104 to determine the false alarm indicative of a patient monitoring data 116, which may not match with any of the data sets stored in the patient specific data bank 142. The user-interface 104 may implement the human in loop system to selectively choose and eliminate the false alarm. The selection of the false alarm may be implemented by providing an input in form of Boolean values. In an embodiment, if the input value is numerical zero then it may indicate a false alarm and if the input value is numerical one then it may indicate a true alarm. The selected patient monitoring data indicative of the false alarms are then stored 806 in the patient specific data bank 142 and modulated.

Figure 9:
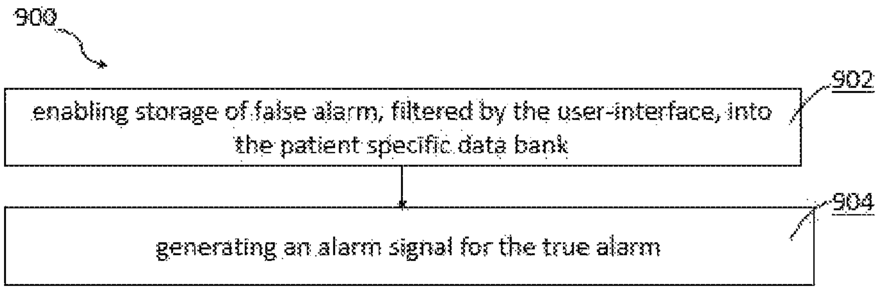
FIG. 9 illustrates a flow chart for the method of filtering the false alarm from the true alarm by the user-interface.

In accordance with an aspect of the disclosure, FIG. 9 illustrates a flow chart 900 for the method of filtering the false alarm from the true alarm by the user-interface 104 and further process of storing the false alarm in form of data sets in the patient specific data bank 142. The processor 124 may enable 902 the storage of the filtered false alarm into the patient specific data bank 142. Once the false alarm and the related data may get stored in the patient specific data bank 142, the processor 124 may generate 904 an alarm signal for a true alarm.

In accordance with another aspect of the disclosure provides non-transitory data memory 126 encoding one or more executable routines, which, when executed by a data processing device 120, cause the data processing device 120 to perform acts comprising: receiving a patient monitoring data 116 from a patient monitoring device 102 and then processing the received patient monitoring data 116 to determine a false alarm generated by the patient monitoring device 102 and then comparing one or more data sets stored in a patient specific data bank 142 with the patient monitoring data 116. Then filtering a false alarm from a true alarm enabled by a user-interface.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that performs particular task and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms “component,” “system,” “platform,” “interface,” and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In accordance with an aspect of the disclosure, respective components can execute from various computer readable media having various data structures stored thereon. The components can communicate via local and/or remote processes such as in accordance with a signal having one or more data packets/data sets (e.g., data from one component interacting with another component in a local system, distributed system, and/or across a network such as the Internet with other systems via the signal). In accordance with an another aspect of the disclosure, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In accordance with an another aspect of the disclosure, a component can emulate an electronic component via a virtual machine, e.g., within a cloud computing system.

In addition, the term “or” is intended to mean an inclusive “or” rather than an exclusive “or.” That is, unless specified otherwise, or clear from context, “X employs A or B” is intended to mean any of the natural inclusive permutations. That is, if X employs A; X employs B; or X employs both A and B, then “X employs A or B” is satisfied under any of the foregoing instances. Moreover, articles “a” and “an” as used in the subject specification and annexed drawings should generally be construed to mean “one or more” unless specified otherwise or clear from context to be directed to a singular form. As used herein, the terms “example” and/or “exemplary” are utilized to mean serving as an example, instance, or illustration and are intended to be non-limiting. For the avoidance of doubt, the subject matter disclosed herein is not limited by such examples. In addition, any aspect or design described herein as an “example” and/or “exemplary” is not necessarily to be construed as preferred or advantageous over other aspects or designs, nor is it meant to preclude equivalent exemplary structures and techniques known to those of ordinary skill in the art.

As it is employed in the subject specification, the term “processor” can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as “store,” “storage,” “data store,” data storage,” “database,” and substantially any other information storage component relevant to operation and functionality of a component are utilized to refer to “memory components,” entities embodied in a “memory,” or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms “includes,” “has,” “possesses,” and the like are used in the detailed description, claims, appendices and drawings such terms are intended to be inclusive in a manner similar to the term “comprising” as “comprising” is interpreted when employed as a transitional word in a claim. The descriptions of the various embodiments have been presented for purposes of illustration but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

This written description uses examples to disclose the invention, including the best mode, and to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A system, comprising:

a patient monitoring device configured to receive patient monitoring data from a subject, wherein the patient monitoring device comprises at least one photodiode or at least one electrode coupled to an analog-to-digital converter (ADC) and at least one of a hardware filter or an amplifier to convert analog signals into digital signals and reduce motion and sensor noise representing patient monitoring parameters comprising electrocardiogram (ECG) data, a heart rate, a blood pressure, an oxygen saturation, a respiration rate, a temperature, or a combination thereof;

a data processing device connected to the patient monitoring device, comprising;

a non-transitory data memory storing a patient-specific data bank indexed by at least patient identity, acquisition time, and originating monitor identifier and configured to store historical physiologic data and selected patient monitoring data indicative of false alarms;

a machine learning module stored in the non-transitory data memory comprising a contrastive neural network adapted to quasi-stationary physiological signals trained by a data sample collection, wherein the machine learning module is configured to (i) extract intermediate representations from the digital signals representing the patient monitoring data and corresponding historical physiological data, (ii) compute a contrastive loss between said intermediate representations, and (iii) compare the digital signals representing the patient monitoring data against the historical physiological data and the selected patient monitoring data indicative of the false alarms stored in the patient-specific data bank to distinguish a false alarm from a true alarm based on whether the contrastive loss is less than or greater than a device-side threshold;

a user-interface operatively coupled to the patient monitoring device and the data processing device, configured to:

filter, based on the digital signals and the comparison from the machine learning module, the true alarm from the false alarm in real time; and an attenuation circuit operatively coupled to an alarm annunciator, comprising:

an audio attenuator configured to reduce an audible alarm volume upon determination that the contrastive loss indicates the false alarm;

a visual indicator comprising a light source configured to emit a distinct illumination pattern corresponding to the false alarm condition;

wherein the system is configured to avoid any alarms based on data from another patient by enforcing a match between the patient monitoring data and the historical physiological data, and the selected patient monitoring data indicative of the false alarms indexed to the same patient identity and originating monitor identifier in the patient-specific data bank using the contrastive neural network, and wherein the system is configured to generate alarm conditions according to patient-specific patterns learned by the contrastive neural network rather than applying uniform thresholds across multiple patients.

2. The system of claim 1, wherein the user-interface is configured to receive an input from a user; wherein the user-interface is connected to the patient monitoring device and the data processing device through a wired means or a wireless means; and the user-interface selected patient monitoring data, indicative of the false alarm, is stored in the patient specific data bank as the data set.

3. The system of claim 2, wherein the input is either a Boolean true or a Boolean false.

4. The system of claim 1, wherein the patient specific data bank having the data sets of the subject and the machine learning module compares the data sets with the patient monitoring data to check for the false alarm; wherein, the false alarm indicates the patient monitoring data matches with the data sets stored in the patient specific data bank; and the false alarm is modulated.

5. The system of claim 1, wherein the patient monitoring device and the data processing device are connected to the user-interface and the user-interface is configured to receive the patient monitoring data from the patient monitoring device.

6. The system of claim 1, wherein the contrastive neural network is operably configured to compare at least two intermediate representations obtained from the layers of the contrastive neural network.

7. The system of claim 6, wherein the contrastive training module sends the patient monitoring data to the user-interface to determine the false alarm when a contrastive loss is greater than a threshold value and enables the user-interface to filter the true alarm from the false alarm; and the user-interface determined false alarm is stored in the patient specific data bank.

8. The system of claim 6, wherein the contrastive learning module is configured to receive and compare the at least two intermediate representations to generate a contrastive loss in order to determine the similarities between the at least two intermediate representations.

9. The system of claim 1, wherein the patient monitoring devices including but not limited to an ultrasound device, a CT scanner, an MR machines, an ECG, an oximeter, an infusion pump, a bedside monitor.

10. A method, comprising:

receiving patient monitoring data from a patient monitoring device, wherein the patient monitoring device comprises at least one photodiode or at least one electrode coupled to an analog-to-digital converter (ADC) and at least one of a hardware filter or an amplifier to convert analog signals into digital signals and reduce motion and sensor noise representing patient monitoring parameters comprising electrocardiogram (ECG) data, a heart rate, a blood pressure, an oxygen saturation, a respiration rate, a temperature, or a combination thereof;

storing a patient-specific data bank indexed by at least patient identity, acquisition time, and originating monitor identifier and configured to store historical physiologic data and selected patient monitoring data indicative of false alarms;

filtering, based on the digital signals and a comparison from a machine learning module, a true alarm from a false alarm in real time, wherein the machine learning module comprises a contrastive neural network adapted to quasi-stationary physiological signals trained by a data sample collection, wherein the machine learning module is configured to (i) extract intermediate representations from the digital signals representing the patient monitoring data and corresponding historical physiological data, (ii) compute a contrastive loss between said intermediate representations, and (iii) compare the digital signals representing the patient monitoring data against the historical physiological data and the selected patient monitoring data indicative of the false alarms stored in the patient-specific data bank to distinguish the false alarm from the true alarm based on whether the contrastive loss is less than or greater than a device-side threshold;

reducing an audible alarm volume upon determination that the contrastive loss indicates the false alarm;

emitting a distinct illumination pattern corresponding to the false alarm condition;

wherein the method avoids any alarms based on data from another patient by enforcing a match between the patient monitoring data and the historical physiological data and the selected patient monitoring data indicative of the false alarms indexed to the same patient identity and originating monitor identifier in the patient-specific data bank using the contrastive neural network, and wherein the method generates alarm conditions according to patient-specific patterns learned by the contrastive neural network rather than applying uniform thresholds across multiple patients.

11. The method of claim 10, wherein processing the received patient monitoring data comprises:

extracting at least two intermediate representations from a contrastive neural network of a machine learning module;

receiving the at least two intermediate representations by the contrastive neural network for comparison; and determining a contrastive loss.

12. The method of claim 10, wherein the comparing one or more data sets stored in the patient specific data bank with the patient monitoring data comprises:

determining the false alarm when the patient monitoring data matches with a data set stored in the patient specific data bank;

sending the patient monitoring data to the user-interface to determine the false alarm for the patient monitoring data when contrastive loss is greater than a threshold value; and storing the patient monitoring data, indicative of the false alarm determined by the user-interface into the patient specific data bank.

13. The method of claim 10, wherein the filtering the false alarm from the true alarm by the user-interface comprising:

enabling storage of the false alarm, filtered by the user-interface, in the patient specific data bank; and generating and reporting an alarm signal for the true alarm.

14. A non-transitory data memory encoding one or more executable routines, which, when executed by a data processing device, cause the data processing device to perform acts comprising:

receiving a patient monitoring data from a patient monitoring device, wherein the patient monitoring device comprises at least one photodiode or at least one electrode coupled to an analog-to-digital converter (ADC) and at least one of a hardware filter or an amplifier to convert analog signals into digital signals and reduce motion and sensor noise, wherein the patient monitoring data comprises patient monitoring parameters comprising electrocardiogram (ECG) data, a heart rate, a blood pressure, an oxygen saturation, a respiration rate, a temperature, or a combination thereof;

storing a patient-specific data bank indexed by at least patient identity, acquisition time, and originating monitor identifier and configured to store historical physiologic data and selected patient monitoring data indicative of false alarms;

filtering, based on the digital signals and a comparison from a machine learning module, a true alarm from a false alarm in real time, wherein the machine learning module comprises a contrastive neural network adapted to quasi-stationary physiological signals trained by a data sample collection, wherein the machine learning module is configured to (i) extract intermediate representations from the digital signals representing the patient monitoring data and corresponding historical physiological data, (ii) compute a contrastive loss between said intermediate representations, and (iii) compare the digital signals representing the patient monitoring data against the historical physiological data and the selected patient monitoring data indicative of the false alarms stored in the patient-specific data bank to distinguish the false alarm from the true alarm based on whether the contrastive loss is less than or greater than a device-side threshold;

reducing an audible alarm volume upon determination that the contrastive loss indicates the false alarm; and emitting a distinct illumination pattern corresponding to the false alarm condition;

wherein the method avoids any alarms based on data from another patient by enforcing a match between the patient monitoring data and the historical physiological data, and the selected patient monitoring data indicative of the false alarms indexed to the same patient identity and originating monitor identifier in the patient-specific data bank using the contrastive neural network, and wherein the method generates alarm conditions according to patient-specific patterns learned by the contrastive neural network rather than applying uniform thresholds across multiple patients.

* * * * *